United States Patent
Norton et al.

(10) Patent No.: US 10,980,532 B2
(45) Date of Patent: Apr. 20, 2021

(54) SUTURE PASSER/RETRIEVER

(71) Applicant: Biomet Sports Medicine, LLC, Warsaw, IN (US)

(72) Inventors: Daniel R. Norton, Warsaw, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 140 days.

(21) Appl. No.: 16/312,592

(22) PCT Filed: Jul. 6, 2017

(86) PCT No.: PCT/US2017/040834
§ 371 (c)(1),
(2) Date: Dec. 21, 2018

(87) PCT Pub. No.: WO2018/009613
PCT Pub. Date: Jan. 11, 2018

(65) Prior Publication Data
US 2019/0159772 A1    May 30, 2019

Related U.S. Application Data

(60) Provisional application No. 62/359,857, filed on Jul. 8, 2016.

(51) Int. Cl.
| | |
|---|---|
| *A61B 17/04* | (2006.01) |
| *A61B 17/00* | (2006.01) |
| *A61B 17/06* | (2006.01) |

(52) U.S. Cl.
CPC ...... *A61B 17/0485* (2013.01); *A61B 17/0469* (2013.01); *A61B 17/0482* (2013.01);
(Continued)

(58) Field of Classification Search
CPC ............ A61B 17/0485; A61B 17/0469; A61B 17/0482; A61B 2017/00349;
(Continued)

(56) References Cited

U.S. PATENT DOCUMENTS 6,936,054 B2 * 8/2005 Chu .................... A61B 17/0469
606/144
7,637,918 B2 * 12/2009 Dant .................. A61B 17/0469
606/144

(Continued)

FOREIGN PATENT DOCUMENTS

| EP | 2456364 A2 | 5/2012 |
|---|---|---|
| WO | WO-2011008607 A1 | 1/2011 |
| WO | WO-2018009613 A1 | 1/2018 |

OTHER PUBLICATIONS

"International Application Serial No. PCT/US2017/040834, International Search Report dated Sep. 15, 2017", 6 pgs.
(Continued)

*Primary Examiner* — Julian W Woo
(74) *Attorney, Agent, or Firm* — Schwegman Lundberg & Woessner, P.A.

(57) ABSTRACT

A suture passer and a method with the suture passer can include a first needle extending along a first longitudinal axis. The first needle can have a sharp tip and a first hook member configured to grasp a portion of a suture. The suture passer can include a shaft extending along a second longitudinal axis. The shaft can have an eyelet that intersects with the first longitudinal axis of the first needle. The suture passer can also have an actuation mechanism coupled to the first needle, and the method can include actuating the actuation mechanism to move the first needle to a position in which the first needle's sharp tip extends through the eyelet, and releasing the actuation mechanism to move the
(Continued)

first needle to a position in which the first needle's sharp tip is a spaced apart a distance proximal of the eyelet.

16 Claims, 11 Drawing Sheets

(52) U.S. Cl.
CPC ............... *A61B 2017/0042* (2013.01); *A61B 2017/00349* (2013.01); *A61B 2017/00991* (2013.01); *A61B 2017/0608* (2013.01); *A61B 2017/06023* (2013.01); *A61B 2017/06042* (2013.01); *A61B 2017/06076* (2013.01)

(58) Field of Classification Search
CPC .. A61B 2017/06023; A61B 2017/0042; A61B 2017/00991; A61B 2017/06042; A61B 2017/06076; A61B 2017/0608
See application file for complete search history.

(56) References Cited

U.S. PATENT DOCUMENTS

| | | | | |
|---|---|---|---|---|
| 7,883,519 | B2* | 2/2011 | Oren | A61B 17/06109 |
| | | | | 606/148 |
| 8,066,718 | B2* | 11/2011 | Weisel | A61B 17/0469 |
| | | | | 606/139 |
| 9,445,807 | B2* | 9/2016 | Brecher | A61B 17/0469 |
| 2002/0198542 | A1 | 12/2002 | Yamamoto et al. | |
| 2009/0131956 | A1 | 5/2009 | Dewey | |
| 2014/0236191 | A1 | 8/2014 | Stone et al. | |
| 2015/0073441 | A1 | 3/2015 | Fallin et al. | |

OTHER PUBLICATIONS

"International Application Serial No. PCT/US2017/040834, Written Opinion dated Sep. 15, 2017", 8 pgs.

"European Application Serial No. 17740239.3, Response filed Sep. 9, 2019 to Office Action dated Feb. 26, 2019", 15 pgs.

* cited by examiner

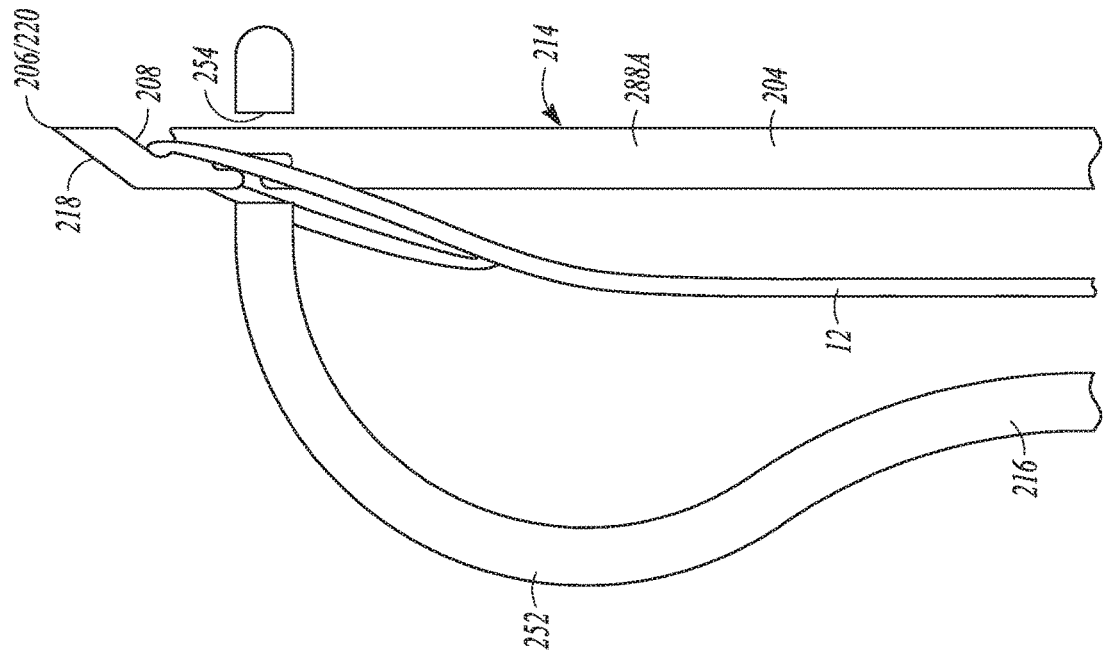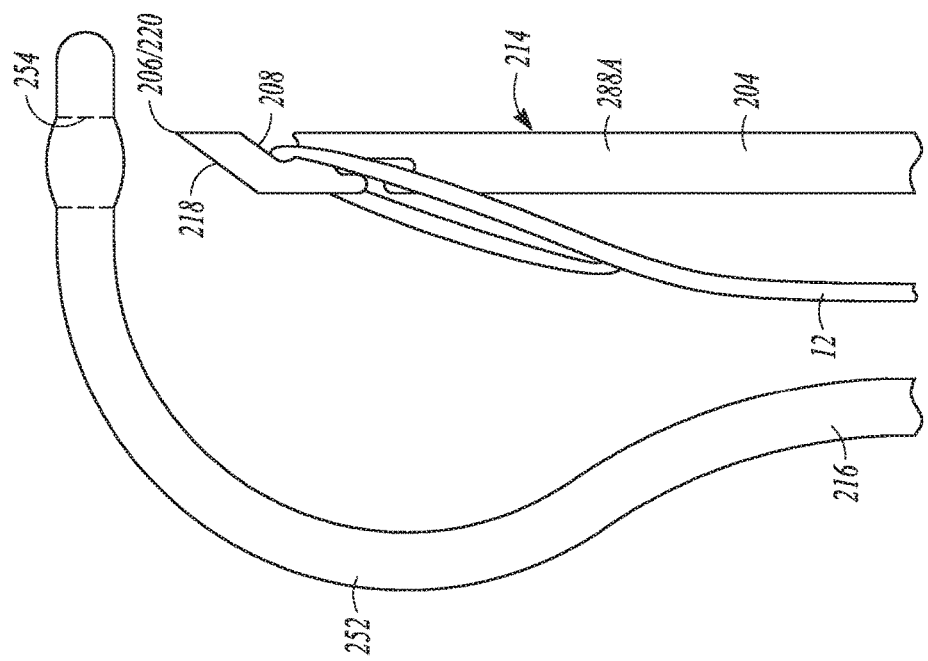

SUTURE PASSER/RETRIEVER

CROSS-REFERENCE TO RELATED APPLICATION(S)

The present application is a U.S. National Stage Application under 35 U.S.C. 371 from International Application Serial No. PCT/US2017/040834, filed on Jul. 6, 2017, and published as WO 2018/009613 A1 on Jan. 11, 2018, which claims the benefit of the filing date of U.S. Provisional Application No. 62/359,857, filed Jul. 8, 2016 and titled "Suture Passer/Retriever", the benefit of priority of each of which is claimed hereby, and the disclosures of each of which is hereby incorporated by reference herein.

FIELD OF THE DISCLOSURE

The present disclosure relates to passing a suture through tissue through two locations and retrieving the suture with one device and without pulling the device out of the joint space.

BACKGROUND

Soft tissue repair can be affected using different suture constructs, in addition to other mechanisms. As an example, a tear of a patient's soft tissue can be reduced and repaired using a stitch or multiple stitches. Yet, appropriately forming a stitch across a tear in soft tissue might require, amongst other things, multiple transcutaneous portals through the patient's skin and tissue and/or the use of multiple tools and sutures to form the stitch. Current methods and tools for reducing a soft-tissue tear in this manner can be cumbersome.

The present disclosure therefore provides unique suture passing devices and methods that improve upon existing technology.

SUMMARY

To better illustrate the system disclosed herein, a non-limiting list of examples is provided here:

Example 1 provides a suture passer comprising a first needle extending along a first longitudinal axis, wherein the first needle has a sharp tip and a first hook member configured to grasp a portion of a suture, a shaft extending along a second longitudinal axis, wherein the shaft has an eyelet that intersects with the first longitudinal axis of the first needle, and an actuation mechanism coupled to the first needle, wherein actuating the actuation mechanism moves the first needle to a position in which the first needle's sharp tip extends through the eyelet, and releasing the actuation mechanism moves the first needle to a position in which the first needle's sharp tip is a spaced apart a distance proximal of the eyelet.

In Example 2, the suture passer of Example 1 can optionally include wherein the shaft comprises a second needle with a sharp tip.

In Example 3, the suture passer of any combination of Examples 1-2 can optionally include wherein the shaft comprises a first straight section extending along the second longitudinal axis, and a second curved section diverging from the second longitudinal axis.

In Example 4, the suture passer of Example 3 can optionally include wherein the eyelet is located on the second curved section of the shaft.

In Example 5, the suture passer of any combination of Examples 1-4 can optionally include wherein the eyelet comprises at least a first opening that is configured to retain a portion of the suture therein.

In Example 6, the suture passer of any combination of Examples 1-5 can optionally include wherein the first needle comprises a second hook member configured to grasp a portion of the suture.

In Example 7, the suture passer of Example 6 can optionally include wherein the first hook member is positioned on a first side of the first needle, and the second hook member is positioned on a second side of the first needle.

In Example 8, the suture passer of any combination of Examples 1-6 can optionally include wherein the first longitudinal axis is substantially parallel to the second longitudinal axis.

Example 9 provides a method of repairing soft tissue comprising positioning an eyelet of a suture passer at a first position relative to a tear in soft tissue of a patient, the eyelet being located on a shaft that extends along a first longitudinal axis, engaging suture with a first needle of the suture passer, the needle having a sharp tip and a needle body that extends along a second longitudinal axis, puncturing the soft tissue with the sharp tip of the needle along a first path through the tissue, and subsequently moving the first needle and the suture engaged thereto through the eyelet so that the suture couples to the shaft, withdrawing the first needle from the eyelet and through the soft tissue along the first path while leaving the suture coupled to the shaft, moving the eyelet from the first position to a second position relative to the tear in the soft tissue, puncturing the soft tissue with the sharp tip of the needle along a second path through the tissue, and subsequently (i) moving the first needle through the eyelet, and (ii) capturing the suture with the first needle and withdrawing the suture through the soft tissue along the second path using the first needle, and reducing the tear in the soft tissue using the suture.

Example 10, the method of Example 9 can optionally further comprise engaging the suture with a first hook member of the first needle, and moving the first needle and the suture engaged thereto by way of the hook member through the eyelet so that the suture couples to the shaft.

In Example 11, the method of Example 10 can optionally further comprise capturing the suture with a second hook member of the first needle, and withdrawing the suture through the soft tissue along the second path by moving the first needle with the suture attached thereto by way of the second hook member through the soft tissue along the second path.

Example 12, the method of any combination of Examples 9-11 can optionally include wherein the first longitudinal axis is substantially parallel to the second longitudinal axis.

Example 13, the method of any combination of Examples 9-11 can optionally include wherein the shaft comprises a first straight section extending along the second longitudinal axis, and a second curved section diverging from the second longitudinal axis.

In Example 14, the method of Example 13 can optionally include wherein the eyelet is located on the second curved section of the shaft.

In Example 15, the method of any combination of Examples 9-14 can optionally further comprise rotating the first needle within the eyelet prior to withdrawing the first needle from the eyelet.

In Example 16, the method of any combination of Examples 9-15 can optionally further comprise engaging a portion of the suture with an opening in the eyelet to couple the suture to the eyelet.

Example 17 provides a suture passer comprising a first needle extending along a first longitudinal axis, wherein the first needle has a sharp tip and a first hook member configured to grasp a portion of a suture, a shaft extending along a second longitudinal axis, wherein the shaft has an eyelet that intersects with the first longitudinal axis of the first needle, and an actuation mechanism coupled to the first needle, wherein the actuation mechanism is configured to rotate the first needle about the first longitudinal axis, and wherein actuating the actuation mechanism moves the first needle to a position in which the first needle's sharp tip extends through the eyelet, and releasing the actuation mechanism moves the first needle to a position in which the first needle's sharp tip is a spaced apart a distance proximal of the eyelet.

Example 18, the suture passer of Example 17 can optionally include wherein the shaft comprises a first straight section extending along the second longitudinal axis, and a second curved section diverging from the second longitudinal axis.

In Example 19, the suture passer of Example 18 can optionally include wherein the eyelet is located on the second curved section of the shaft.

In Example 20, the suture passer of any combination of Examples 17-19 can optionally include wherein the first needle is rotatable when positioned inside the eyelet to place the first needle in a removal orientation.

BRIEF DESCRIPTION OF THE FIGURES

The above-mentioned and other features and advantages of the disclosure, and the manner of attaining them, will become more apparent and the disclosure itself will be better understood by reference to the following description of examples taken in conjunction with the accompanying drawings, wherein:

FIGS. 9A-F illustrate an alternate movable needle used with an alternate suture passer, according to an example of the disclosure.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

Figure 1:
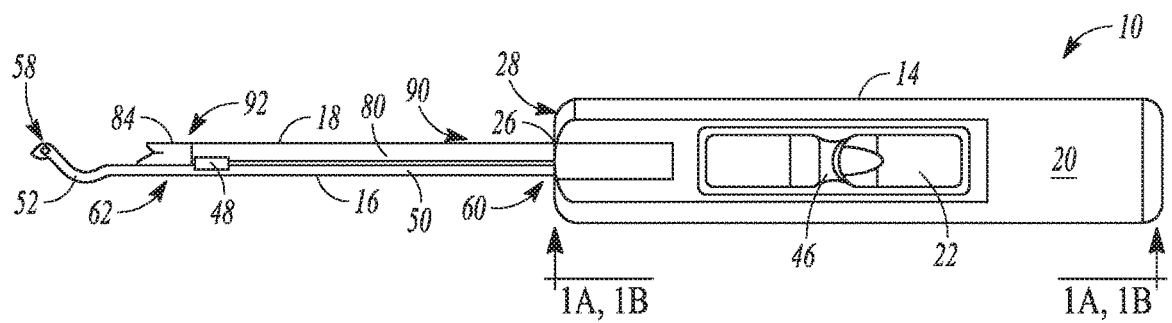
FIG. 1 is a side view of a suture passer, according to an example of the disclosure.

In describing the examples of the disclosure illustrated and to be described with respect to the drawings, specific terminology will be used for the sake of clarity. However, the disclosure is not intended to be limited to any specific terms used herein, and it is to be understood that each specific term includes all technical equivalents.

The device of the present disclosure can contain a blunt or sharp needle with an eyelet. A sharp actuating needle with two (2) opposing cutouts can run in-line with the eyelet. The proximal cutout can be designed to hold onto a suture and push the suture distally. The distal cutout can be designed to grab a suture from the eyelet and pull it proximally.

The device of the present disclosure can allow the user to position the eyelet through or under tissue. Suture can be locked into the proximal cutout on the actuating needle. The needle can be actuated so as to pierce tissue with the actuating needle and lock the suture into the distal eyelet. The distal eyelet can then be moved to a second location relative to the tissue. The actuating needle can then be used to pierce tissue in a second location and retrieve the suture from the eyelet in the distal cutout of the actuating needle.

A variation of the foregoing exemplary device can have an eyelet geometry that can grab suture toward one side of the eyelet instead of in the middle. The actuating pin can be configured to rotate 180 degrees each time it is actuated.

The device of the present disclosure is the only known pass/retrieve device that can create a mattress stitch without being removed from the joint.

The following description of various embodiments is merely exemplary in nature and is not intended to limit the present disclosure, its application, or uses. It should be understood that throughout the drawings, corresponding reference numerals indicate like or corresponding parts and features. With reference to the drawings, various methods and apparatuses are disclosed according to the present teachings for passing a suture through an exemplary soft tissue, such as a labrum within a glenohumeral joint. However, the various apparatuses and methods can also be used for a plurality of procedures and to repair other soft tissues in the anatomy, such as those damaged through trauma, overuse, surgical intervention, or disease. Therefore, the various apparatuses and methods should not be limited to use only for tissue damage in the glenohumeral area. For example, the various instruments can be used to affix or hold a hamstring, Achilles tendon allograft, other soft tissue, or any other appropriate portion. In addition, although various embodiments may illustrate a suture knot for securing a selected tissue, it will be understood that any mode of securing the afflicted tissue can be used. Therefore, it will be understood that the following discussions are not intended to limit the scope of the present teachings or claims herein.

Referring now to the drawings, a suture passing instrument is generally indicated by reference number 10. Suture passing instrument 10 can be operable for passing a suture 12 through the labrum to assist in repairing the joint. Unless specifically mentioned, the various components of the suture passing instrument 10 can be made of a biocompatible material, such as stainless steel, to allow for sterilization using chemicals or autoclaving. It is understood that select components described herein can be made from non-stainless steel materials and therefore those select components may not be suitable for all sterilization techniques due to heat sensitivity or chemical sensitivity of the materials. Moreover, suture passing instrument 10 can be a single-use (i.e., disposable) or can be a standardized instrument that can be fitted with removable and replaceable components.

Figure 1A:
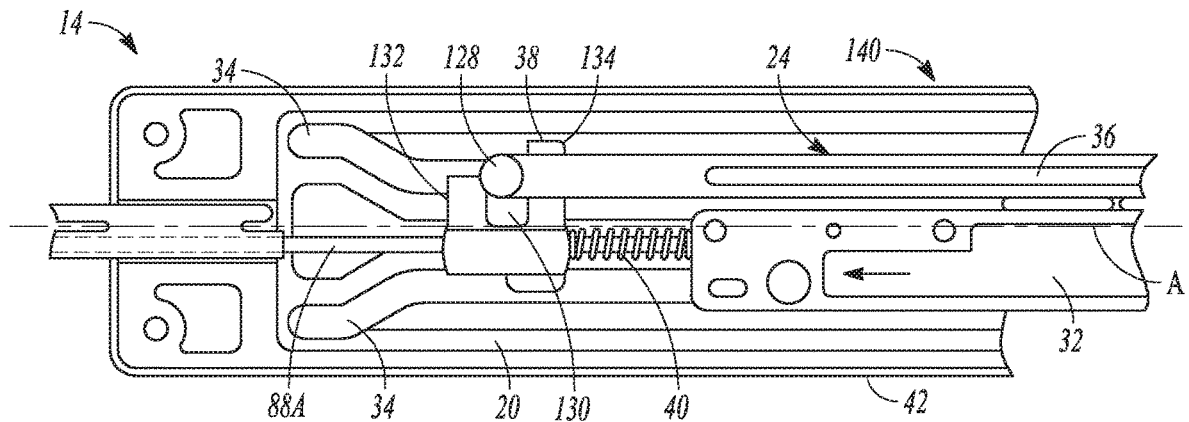
FIG. 1A is a close-up view of a handle of the suture passer of FIG. 1 with its actuator in a first, retracted position.
Figure 1B:
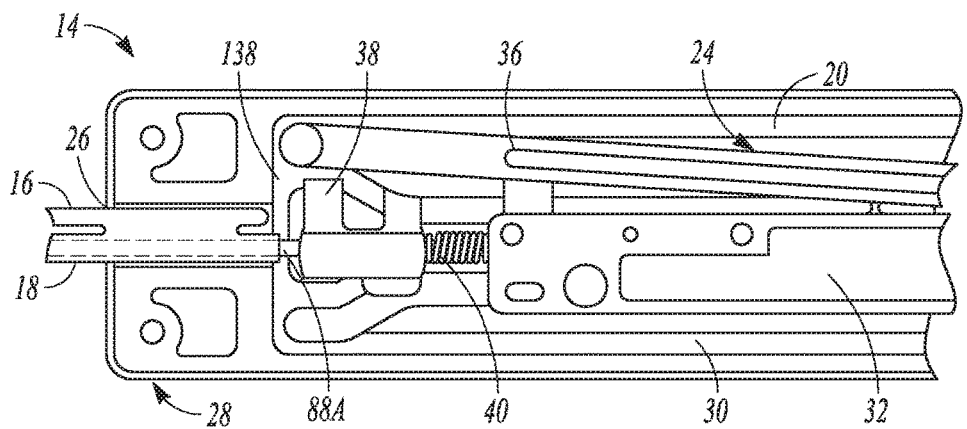
FIG. 1B is a close-up view of the handle of the suture passer of FIG. 1 with its actuator in a second, extended position.

With particular reference to FIGS. 1, 1A, and 1B, suture passing instrument 10 can include an operation handle 14, an elongated shaft or fixed needle member 16, and a suture holder assembly 18. The operation handle 14 can further include a handle body 20, an actuator 22 disposed thereon, and a slider mechanism 24 disposed therein. As shown and described, the handle body 20 can include at least one opening 26 at a distal end 28 for receiving the fixed needle member 16 and the suture holder assembly 18, a central cavity 30 for receipt of a first slide member 32, and a plurality of curved channels 34 integrally formed in the handle body 20 for receipt of a second slide member 36. The slider mechanism 24 can include the pivotally attached first and second slide members 32, 36, a c-shaped translation member 38, and a spring 40. The first and second slide members 32, 36 can move longitudinally along the central cavity 30 and curved channels 34, respectively. Notably, the curved channels 34 can be mirrored about a center axis, A, of the operation handle 14 to allow for a single design for right-handed and left-handed handles. Furthermore, the handle body 20 can be formed from any biocompatible material (e.g., metal or polymer) and can also include a textured exterior surface 42 (e.g., knurl, padding) to provide comfort and/or grip for the operator.

The actuator 22 can be a trigger member operable for actuating the slider mechanism 24 in a longitudinal direction along the handle body 20 from a first or retracted position (as shown in FIGS. 1 and 1A) to a second or extended position (as shown in FIG. 1B). The actuator 22 can define a centrally-raised, finger grip portion 46 for assisting an operator in movement between the retracted and extended positions. Although not shown, the actuator 22 can also incorporate the textured exterior surface (e.g., knurl, padding) to provide comfort and/or grip for the operator.

Figure 2:
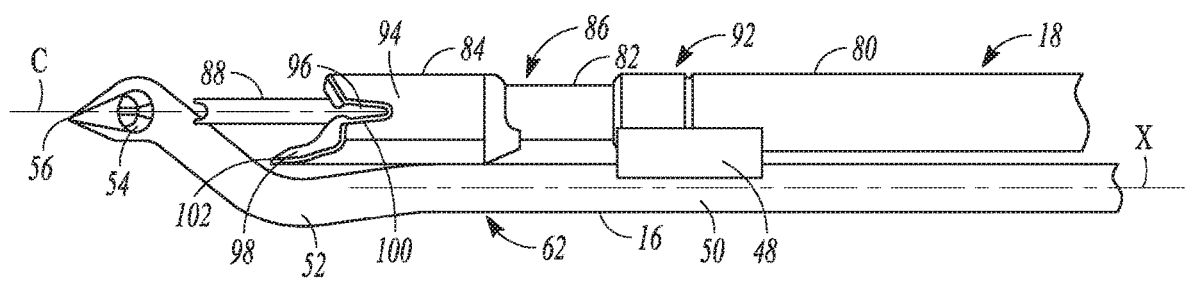
FIG. 2 is a side view of the suture holder assembly and the needle member of the suture passer of FIGS. 1-1B.

With reference now to FIGS. 1 and 2, the fixed needle member 16 and suture holder assembly 18 can extend from the distal end 28 of the handle body 20. Furthermore, the fixed needle member 16 and suture holder assembly 18 can have a connection member 48 located therebetween. Both the fixed needle member 16 and suture holder assembly 18 can be fixedly coupled to the operation handle 14 and the connection member 48 to maintain a parallel relationship and to prevent relative movement therebetween. It should be understood that the connection member 48 can be any device for securing the fixed needle member 16 and the suture holder assembly 18 together, including but not limited to, an adhesive, a weld, and a fastener.

The fixed needle member 16 can include a straight elongated shaft 50, a curved end 52 integrally formed with the elongated shaft 50, a needle eyelet 54 extending through the curved end 52, and a pointed tip 56 at a distal end 58 of the fixed needle member 16. It should be understood that configurations are contemplated where pointed tip 56 can be removed such that curved end 52 is a blunt needle that is designed to abut the tissue to be sutured rather than pierce the tissue. The elongated shaft 50 can extend along a longitudinal axis, X, and can have a first, proximal end 60 extending from the distal end 28 of the handle body 20 and a second, distal end 62 terminating a predetermined distance beyond the connection member 48. The curved end 52 can extend from the second end 62 of the elongated shaft 50 such that a centerline C of the needle eyelet 54 is brought into a coaxial arrangement with a longitudinal axis, Y, of the suture holder assembly 18. As can be seen, the longitudinal axis, X, of the elongated shaft 50 and the longitudinal axis, Y, of the suture holder assembly 18 can be generally parallel to one another along their lengths. Alternative configurations for curved end 52 can include a "pig-tail" shape defined by a right or left helix curve over its length.

Figure 3A:
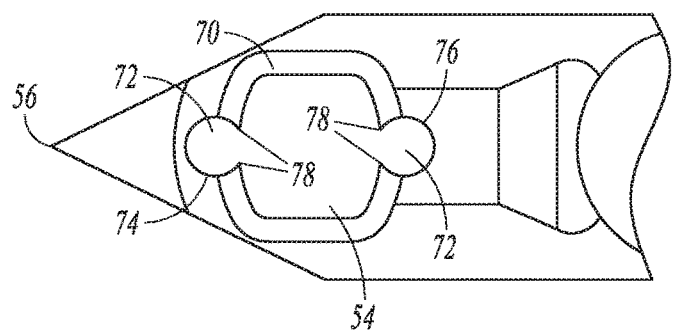
FIG. 3A is a close-up view of the eyelet of the suture passer of FIGS. 1-2.
Figure 3B:
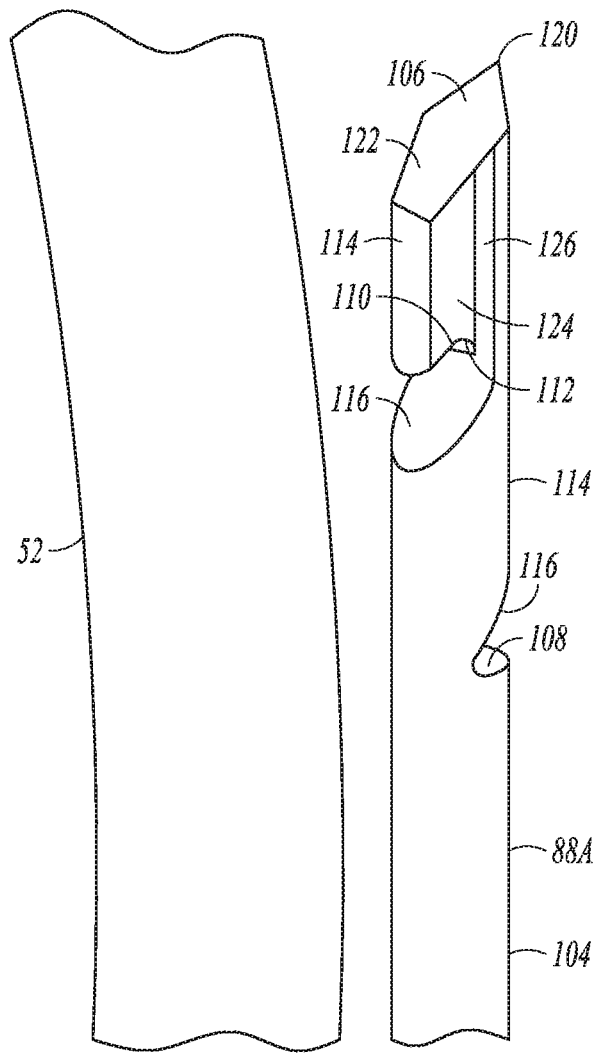
FIGS. 3B-C are close-up views of the movable needle of the suture passer of FIGS. 1-3A.
Figure 3C:
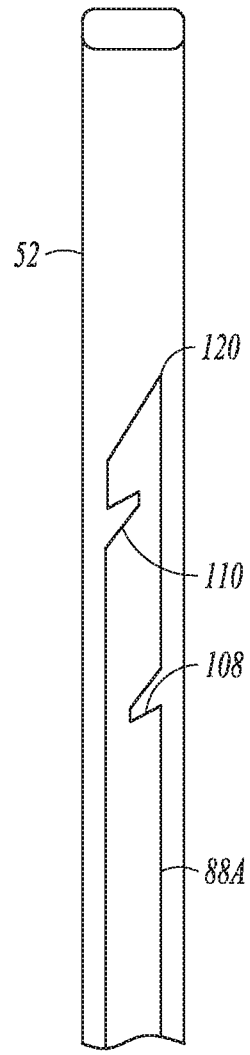
Figure 3D:
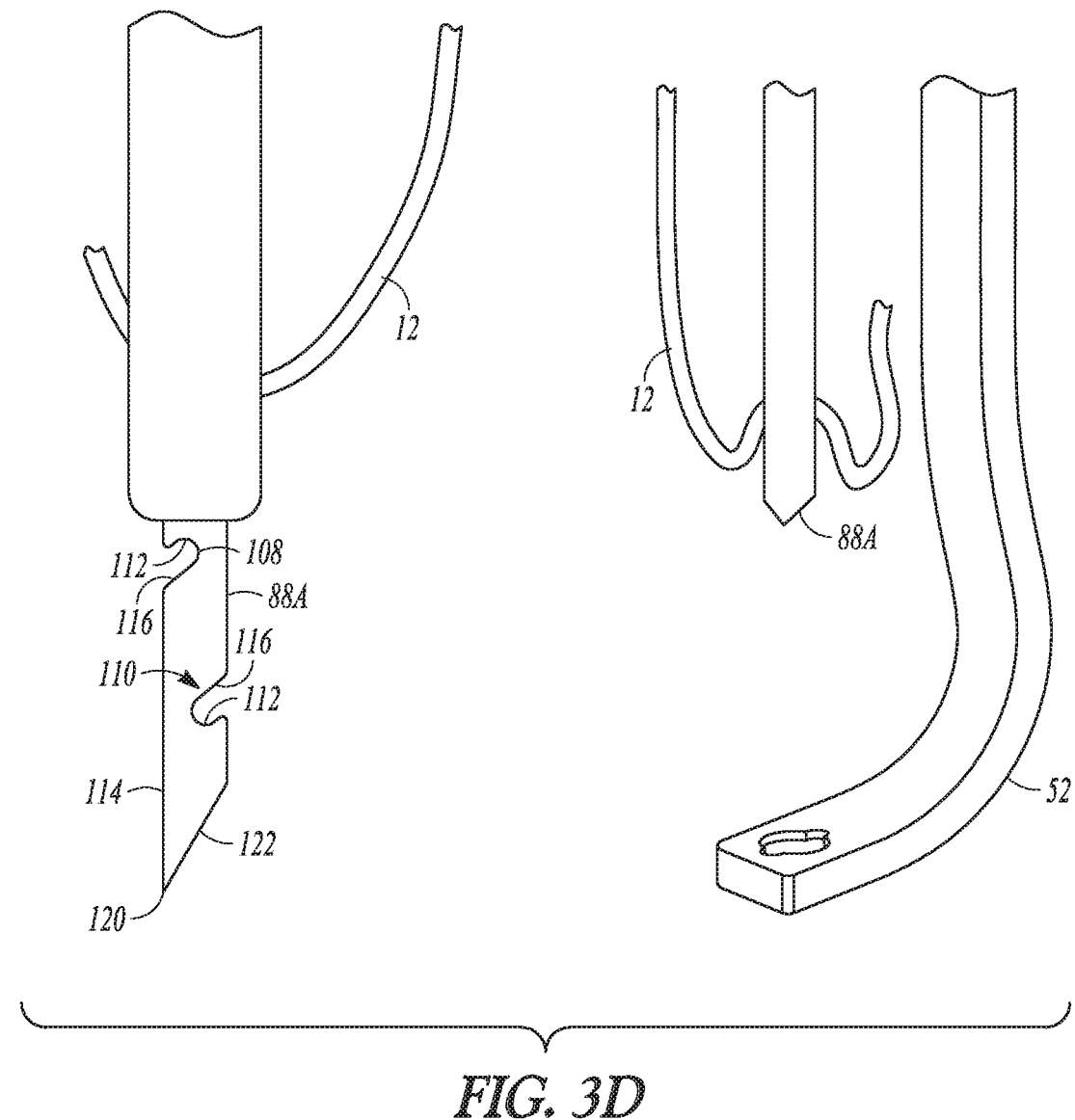
FIG. 3D includes side and perspective views of the movable needle and the curved end of the needle member of the suture passer of FIGS. 1-3C.
Figure 3E:
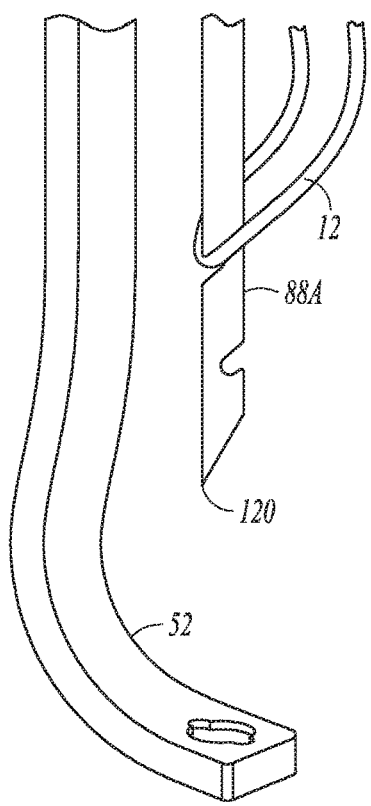
FIG. 3E is a perspective view of the movable needle with a suture attached thereto as the movable needle approaches the eyelet of the suture passer.
Figure 3F:
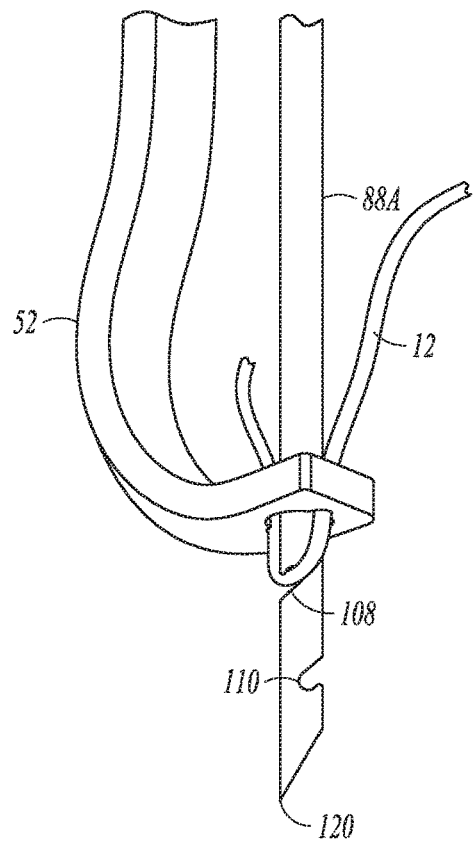
FIG. 3F is a perspective view of the suture being pushed through the eyelet using the movable needle.
Figure 3G:
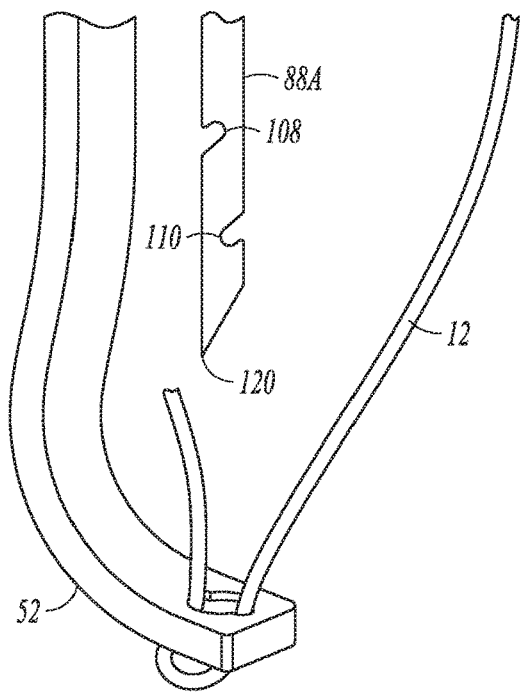
FIG. 3G is a perspective view of the movable needle being withdrawn from the eyelet with the suture still attached to the eyelet.

With particular reference to FIG. 3A, the needle eyelet 54 can define a generally hexagonal periphery 70 symmetrically arranged about a plane extending from the pointed tip 56 and through centerline, C. Furthermore, the needle eyelet 54 can define a pair of opposed semi-circular openings 72 arranged at and extending from distal and proximal ends 74, 76 of the hexagonal periphery 70. The semi-circular openings 72 can have pointed, opposed ends 78 terminating at the hexagonal periphery 70 for gripping the suture 12, as will be described in more detail below.

Referring again to FIGS. 1 and 2, suture holder assembly 18 can include a generally straight tubular shaft 80, a tubular extension rod 82 telescopically received within the tubular shaft 80, a cannulated suture carrier 84 at a distal end 86 of the tubular extension rod 82, and a movable needle 88 telescopically arranged within the cannulated suture carrier 84. The generally tubular shaft 80 can extend along the longitudinal axis, Y, and has a first, proximal end 90 extending from the distal end 28 of the handle body 20 and a second, distal end 92 terminating at the connection member 48. The tubular extension rod 82 can be coupled to or in communication with both the actuator 22 and the cannulated suture carrier 84. Therefore, movement of actuator 22 can cause movement of the tubular extension rod 82, as will be described in more detail below.

Cannulated suture carrier 84 can define a carrier body 94 having a pair of opposing, parallel channels 96, and an extended nose portion 98. The parallel channels 96 can have a predetermined length extending into the carrier body 94 and can have a width for receipt of sutures of various sizes. Accordingly, the parallel channels 96 can have sidewalls 100 that are angled (FIG. 2). The nose portion 98 can extend outwardly from the carrier body 94 in a generally spade-shaped configuration, terminating at a nose tip 102. The nose tip 102 can be located adjacent to the fixed needle member 16. The nose portion 98 can be angled to direct the suture 12 into the parallel channels 96 of the carrier body 94 during loading of the suture 12.

With reference now to FIGS. 3B to 3G, a movable needle 88a is illustrated. Movable needle 88a can serve as a direct replacement for the movable needle 88 illustrated in FIG. 1. Movable needle 88a can define a generally cylindrical needle body 104 that terminates at a needle tip 106. As movable needle 88a is designed to pass through eyelet 54, movable needle 88a is sized to be movably received within the eyelet 54 of the fixed needle member 16. Needle body 104 can include a first recess or hook member 108 and a second recess or hook member 110 extending radially inwardly from an exterior surface 112 thereof. Hook members 108 and 110 can be formed on opposing sides of needle body 104. Hook member 108 can be configured to push suture 12 through eyelet 54, while hook member 110 can be configured to pull suture 12 through eyelet 54. This process will be described in more detail below during description of the operation of suture passing instrument 10. Hook members 108 and 110 can each include a cylindrical surface 112 that extends orthogonal to the cylindrical exterior surface 114 of needle body 104. Cylindrical surfaces 112 can be designed to satisfactorily hold suture 12 therein when suture 12 is being either pushed or pulled by movable needle 88a. Cylindrical surfaces 112 can merge into angled surfaces 116 that extend either toward needle tip 106 (hook member 108) or away from needle tip 106 (hook member 110).

Needle tip 106 can be defined by a planar needle surface 118 that is angled relative to exterior surface 114 and extends from a terminal end 120 of needle tip 106 axially back toward hook member 110. As needle surface 118 extends axially back toward hook member 110, a width of needle surface 118 can radially narrow such that needle surface 118 at least partially defines a ridge 122 extending between hook member 110 and needle tip 106. Ridge 122 can include a pair of planar side surfaces 124 that terminate at the curved exterior surface 114 defined by cylindrical needle body 104. Elongate planar edge surfaces 126 can extend orthogonally outward from planar side surfaces 124 along a length of ridge 122 from hook member 110 to planar needle surface 118. Movable needle 88a can include ridge 122 to reduce the surface area of needle tip 106, which can reduce the amount of trauma to the tissue being sutured during advancement and retraction of movable needle 88a through the tissue. In addition, ridge 122 can allow for ingress of the suture 12 within the eyelet 54 of the fixed needle member 16.

As can be seen from FIGS. 1 through 3G, the movable needle 88a can extend through the tubular extension rod 82 and the tubular shaft 80 for direct connection with the first slide member 32 in the operation handle 14. The spring 40 can extend over the movable needle 88a in the operation handle 14 and abut the first slide member 32. The c-shaped translation member 38 can also extend over the movable needle 88 in the operation handle 14 and can abut the other side of the spring 40 so as to contain the spring 40 between the c-shaped translation member 38 and the first slide member 32. The tubular extension rod 82 can be fixedly attached to the c-shaped translation member 38 opposite the spring 40.

The second slide member 36 can include an extending pin 128 drivingly contacting the c-shaped translation member 38. In the retracted position, the extending pin 128 can be located at a central portion 130 between a short leg 132 and a parallel long leg 134 of the c-shaped translation member 38. When the actuator 22 moves to the extended position, the second slide member 36 can move along the curved channel 34. The extending pin 128 can contact the short leg 132 causing it to move longitudinally, as well. As the second slide member 36 reaches the distal end 28 of the handle body 20, however, the extending pin 128 can curve away from the short leg 132 along the channel 34, removing the longitudinal translation force from the c-shaped translation member 38.

Operation of the suture passing instrument 10 will now be described with reference to the labrum of the glenohumeral joint shown in FIGS. 4 and 4A, and the slider mechanism 24 shown in FIGS. 1A and 1B. The labrum 136 is depicted in detail in FIG. 4A as it is within the glenohumeral joint, T, but it is obstructed from view in the other figures in order to shown positioning of the helix in the tissue. It should be understood that the repair as described herein is being completed on the labrum 136. Initially with the actuator 22 in the retracted position, the appropriately sized suture 12 can be loaded into the parallel channels 96 of the cannulated suture carrier 84. The suture 12 can be loaded transversely to the longitudinal axis, Y, by dragging the suture 12 along the incline of the nose portion 98. The angle of the sidewalls 100 (FIG. 2) can allow the suture 12 to extend within the parallel channels 96 to be removably retained therewith.

Figure 4:
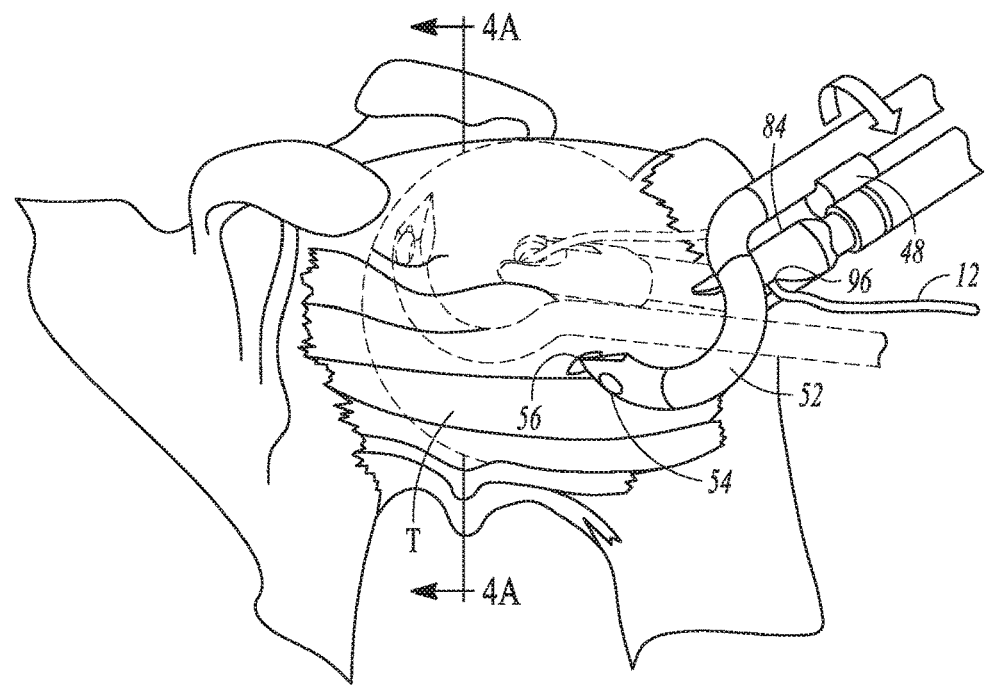
FIGS. 4-4A are perspective views illustrating the suture passer of FIGS. 1-3G being used to repair a soft-tissue tear.
Figure 4A:
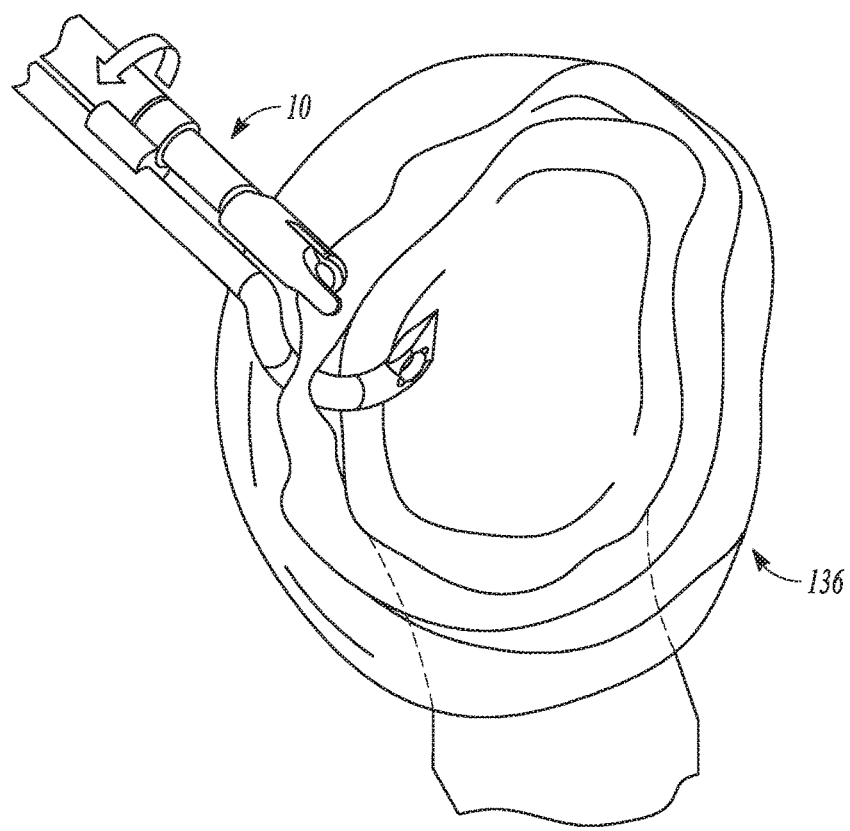
Figure 5:
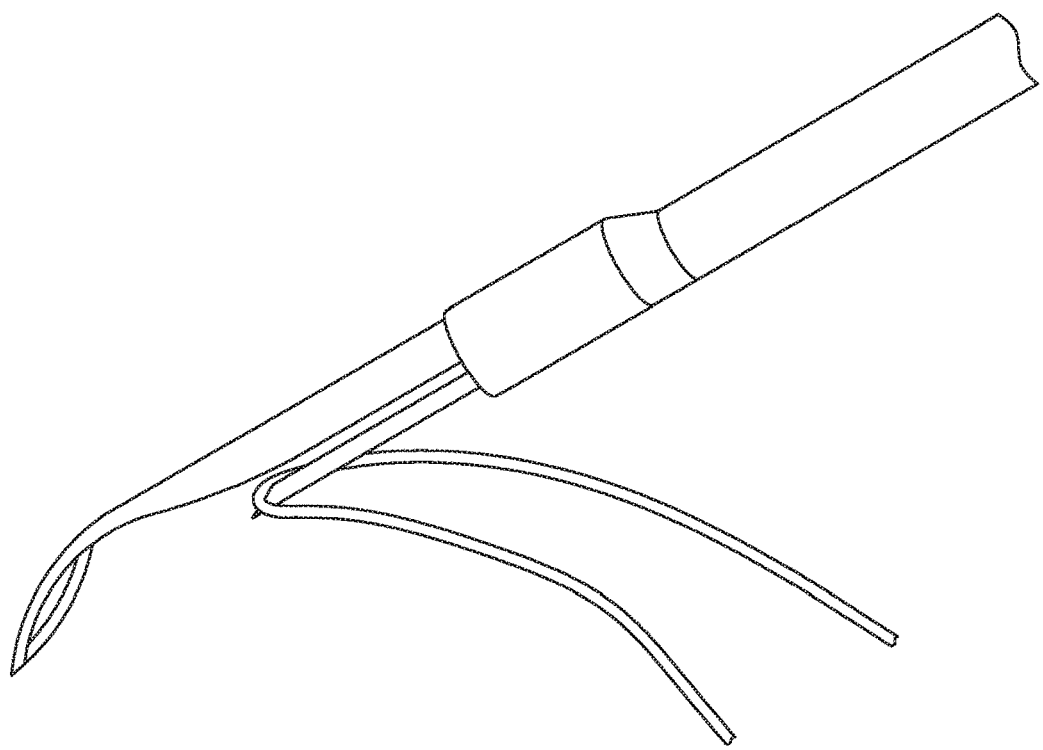
FIGS. 5-8 illustrate other exemplary views of the suture passer according to various aspects of the present teachings.
Figure 6:
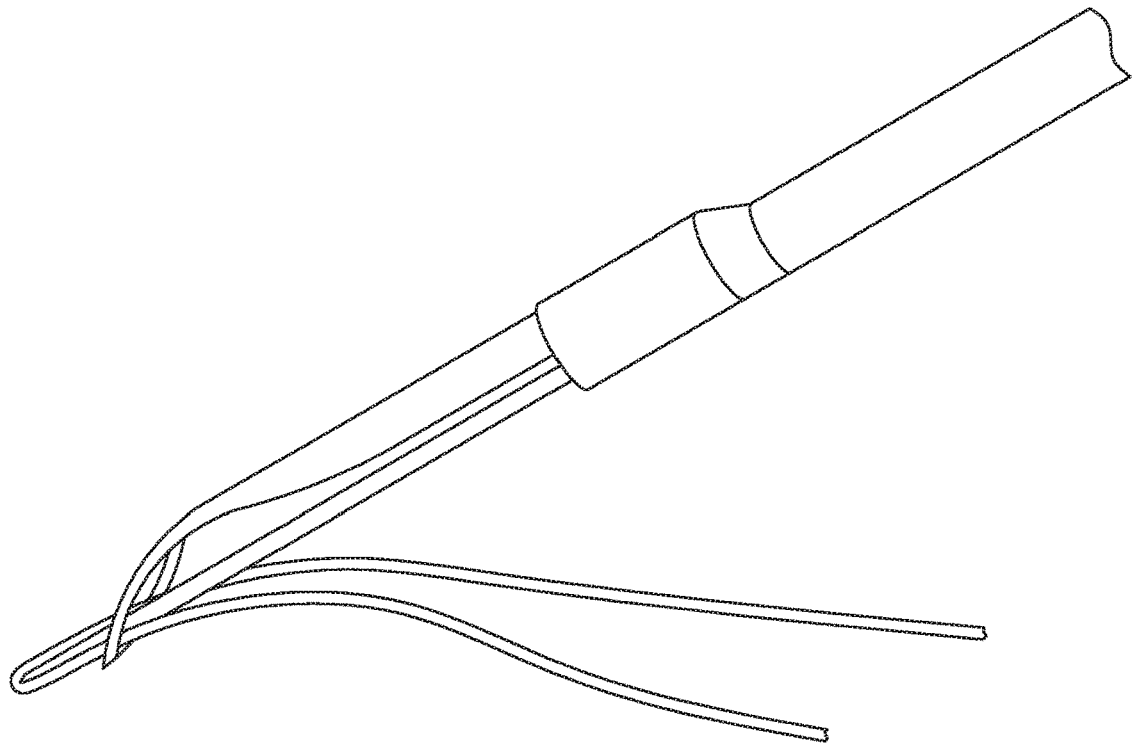
Figure 7:
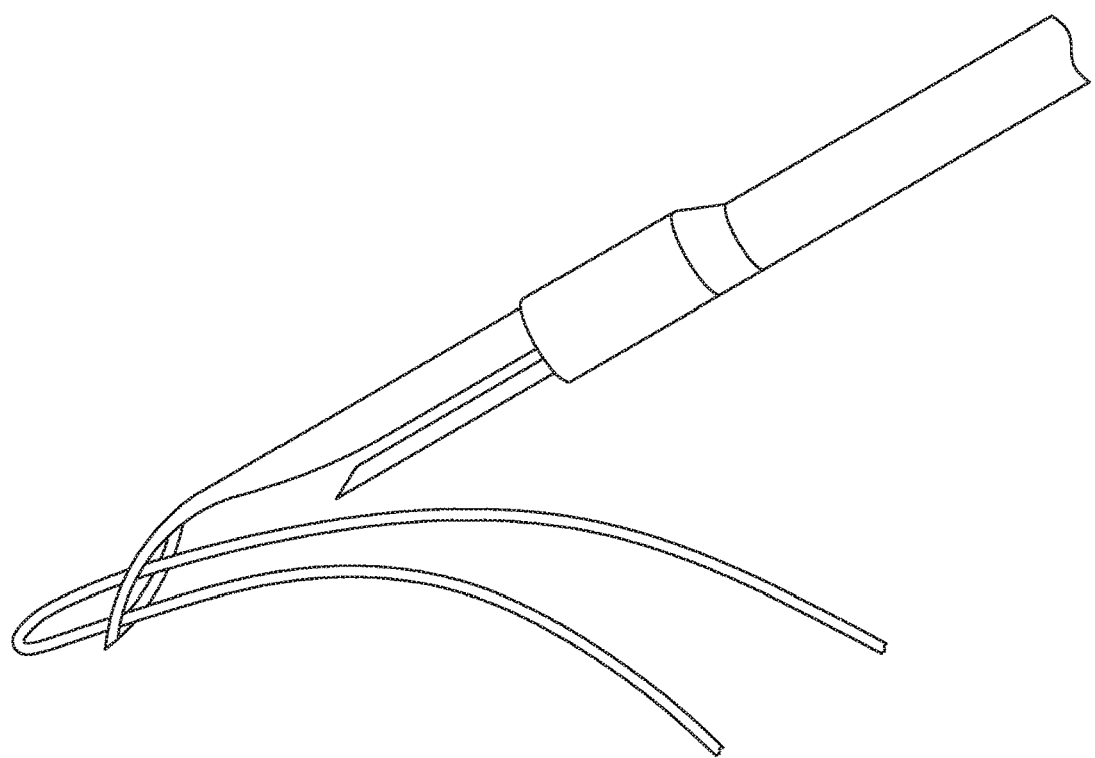
Figure 8:
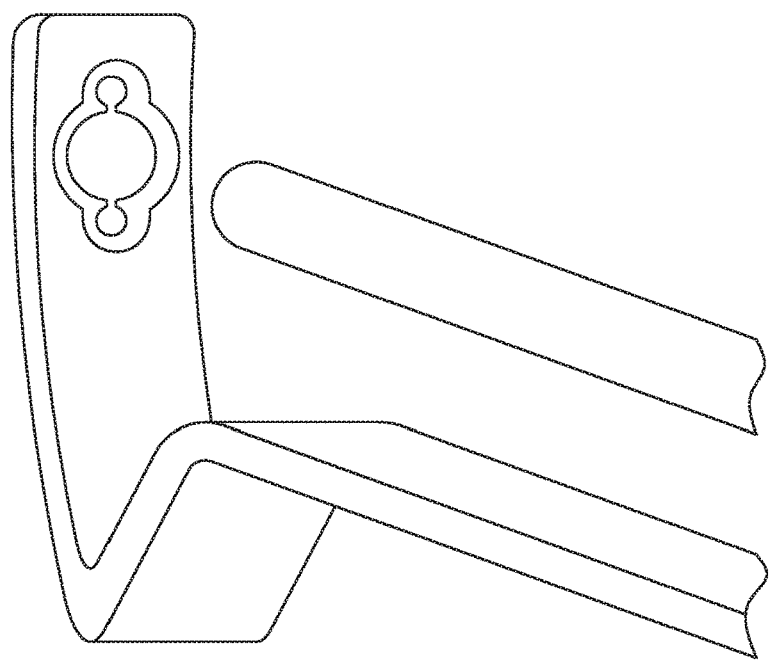

With particular reference to FIGS. 4 and 4A, curved end 52 of fixed needle 16 can be brought into abutting contact with the labrum 136 of the glenohumeral joint T. Curved end 52 can be brought into abutting contact with labrum 136 by either piercing labrum 136, or being placed behind labrum 136 such that eyelet 54 is positioned behind the tissue to be sutured. After the curved end 52 of the fixed needle member 16 is in abutting contact with the labrum 136, the actuator 22 can be moved to the extended position. The actuator 22 can be fixedly attached to the slider mechanism 24, so that longitudinal movement of the actuator 22 to the extended position, in turn, causes movement of the slider mechanism 24. In particular, the actuator 22 an drive the slider mechanism 24 towards the distal end 28 of the handle body 20. This longitudinal movement can cause the first and second slide members 32, 36 to translate in the central cavity 30 and curved channels 34, respectively. As previously described, the extending pin 128 of the second slide member 36 can drivingly move the short leg 132 of the c-shaped translation member 38. The concurrent movement of the first slide member 32 and the c-shaped translation member 38 can cause the tubular extension rod 82 and the movable needle 88a to extend through the tubular shaft 80 at an equivalent speed. Accordingly, the tubular extension rod 82 and movable needle 88a of the suture holder assembly 18 can move distally out of the tubular shaft 80 directing the cannulated suture carrier 84 towards the needle eyelet 54.

As the second slide member 36 reaches the distal end 28 of the handle body 20, the extending pin 128 can curve away from the short leg 132 along the channel 34, removing its longitudinal driving force. The c-shaped translation member 38 can then contact a stop 138 located at the distal end 28 of the handle body 20, preventing any further longitudinal movement of the c-shaped translation member 38 and the tubular extension rod 82. This stopped motion of the c-shaped translation member 38 equates to a stopped motion of the cannulated suture carrier 84 when the nose portion 98 extends over the curved end 52 of the fixed needle member 16 and the cannulated suture carrier 84 extends to a predetermined distance away from the fixed needle member 16.

The first slide member 32 can continue its longitudinal translation through the central cavity 30, compressing the spring 40 as it moves. As should be understood, the movable needle 88a can continue movement with the first slide member 32, which can cause its extension from the tubular extension rod 82 and the cannulated suture carrier 84. In this motion, the hook member 108 can capture the suture 12 retained by the parallel channels 96 of the cannulated suture carrier 84 and can pull the suture 12 out of the channels 96. As movable needle 88a is advanced, needle tip 106 can pass through eyelet 54 and can pierce labrum 136. Movable needle 88a can be advanced to an extent where hook member 108 carrying suture 12 extends entirely through needle eyelet 54, forcing the suture 12 therethrough.

Once within the needle eyelet 54, the suture 12 can be eased towards the semi-circular openings 72 by the tapered shape of the movable needle 88a and by arrangement of the angled shape of the periphery 70. The opposed ends 78 of the semi-circular openings 72 can then receive the suture 12 for retention therewith. It should be understood that the opposed ends 78 might slightly flex as the suture 12 is eased towards the semi-circular openings 72. Furthermore, the opposed ends 78 can "bite" into fibers of the suture 12 to provide the requisite retention for the suture 12.

After the suture 12 extends through the needle eyelet 54 a predetermined distance, the operator can then return the actuator 22 to the retracted position. During retraction, the operator can remove the longitudinal force from the actuator 22 allowing the first slide member 32 to snap back from the distal end 28 of the handle body 20 due to force from the spring 40. The movable needle 88, likewise, can return to its initial position within the cannulated suture carrier 84.

The actuator 22 can be returned to the retracted position by applying a reverse longitudinal force therewith. In particular, the actuator 22 can drive the slider mechanism 24 towards a proximal end 140 of the handle body 20. This longitudinal movement can cause the first and second slide members 32, 36 to translate in a reverse direction in the central cavity 30 and curved channels 34. As the second slide member 36 moves away from the distal end 28 of the handle body 20, the extending pin 128 can curve back towards the c-shaped translation member 38 and drivingly engage the long leg 134 of the c-shaped translation member 38. The concurrent movement of the first slide member 32 and the c-shaped translation member 38 can cause the tubular extension rod 82 and the movable needle 88a to retract into the tubular shaft 80. Accordingly, the cannulated suture carrier 84 can be withdrawn by the reverse movement of the tubular extension rod 82. Notably, however, the suture 12 is captured within the needle eyelet 54.

With suture 12 captured within needle eyelet 54 and extending through labrum 136, a position of fixed needle member 16 can be moved a distance ranging between 2-5 millimeters to another location of labrum 121. Movable needle 18 can then be re-advanced toward eyelet 54 by actuating suture passing instrument 10 as described above. Because fixed needle member 16 has been repositioned to another location of labrum 121, as movable needle 88a passes again though eyelet 54, re-pierces labrum 136 and extends through labrum 136 such that hook member 110 also passes through labrum and grasps suture 12. After suture 12 has been grasped by hook member 110, the operator can then return the actuator 22 to the retracted position to allow movable needle 88a to retract and pull suture 12 back through eyelet 54 and labrum 136 to form a mattress-type stitch. Ends of the suture 12 can then be knotted outside of the surgical opening for a minimally invasive repair.

Although operation of suture passing device 10 has been described above with fixed needle 16 being placed in abutting contact with the tissue to be sutured, it should be understood that fixed needle 16, when configured with the sharpened point of tip 56, can be used to first pierce the ligament T and allow the suture passing instrument 10 to establish an opening within the labrum 136 within the joint T. The movable needle 88a can then be advanced and retracted twice as described above to form the mattress-type stitch.

FIGS. 5-8 illustrate other exemplary views of the suture passing instrument according to various aspects of the present teachings.

FIGS. 9A-F illustrate an alternate movable needle 288a and an alternate curved end 252 of a fixed needle member 216, and the operation of such a movable needle 288a. Similar reference numerals are used for FIGS. 9A-F as for movable needle 88a, except in the 200 series. Further, it is to be understood that movable needle 288a can be used in any of the procedures described above, can have any of the features of movable needle 88a unless set forth differently below, and/or serve as a replacement for movable needle 88a.

Movable needle 288a can define a generally cylindrical needle body 204 that terminates at a needle tip 206. Further, movable needle 288a can be designed to pass through eyelet 254 of alternate curved end 252, similar to as described previously with respect to movable needle 88a. However, movable needle 288a can also be rotatable within eyelet 254 of curved end 252, as described in more detail below.

Needle body 204 can include a first recess or hook member 208 and a second recess or hook member 210 extending radially inwardly. Hook members 208 and 210 can be formed on opposing sides of needle body 204. Hook member 208 can be configured to push suture 12 through eyelet 254, while hook member 210 can be configured to pull suture 12 through eyelet 254. This process will be described in more detail below during description of the operation of the alternate suture passing instrument. Hook member 208 can include a surface 212 that extends orthogonal to the cylindrical exterior surface 214 of needle body 204. Surface 212 can be designed to satisfactorily hold suture 12 therein when suture 12 is being pushed by movable needle 288a. Surface 212 can merge into angled surfaces 216 that extend toward needle tip 206 (hook member 208). In the case of hook member 210, it can be shaped similar to the end of a puzzle piece. As such, hook member 210 can have a small opening 240 that can open into a relatively larger opening 242 for retaining suture 12 within larger opening 242. In an example, small opening 240 can have a maximum width dimension that is slightly less than a diameter of suture 12 so that suture 12 can be squeezed through small opening 240 and into larger opening 242. Larger opening 242 can therefore be designed to satisfactorily hold suture 12 therein when suture 12 is being pulled by movable needle 288a. In another example, small opening 242 can have a maximum width dimension that is slightly greater than a diameter of suture 12.

Needle tip 206 can be defined by a planar needle surface 218 that can be angled relative to exterior surface 214 and extend from a terminal end 220 of needle tip 206 axially back toward hook member 210. As needle surface 218 extends axially back toward hook member 210, a width of needle surface 218 can radially narrow such that needle surface 218 at least partially defines a ridge (not shown) extending between hook member 210 and needle tip 206. The ridge (not shown) can be similar to ridge 122 of movable needle 88a. Movable needle 288a can include the ridge (not shown) to reduce the surface area of needle tip 206, which reduces the amount of trauma to the tissue being sutured during advancement and retraction of movable needle 288a through the tissue. In addition, the ridge (not shown) can allow for ingress of the suture 12 within the eyelet 254 of the fixed needle member 216.

Figure 9C:
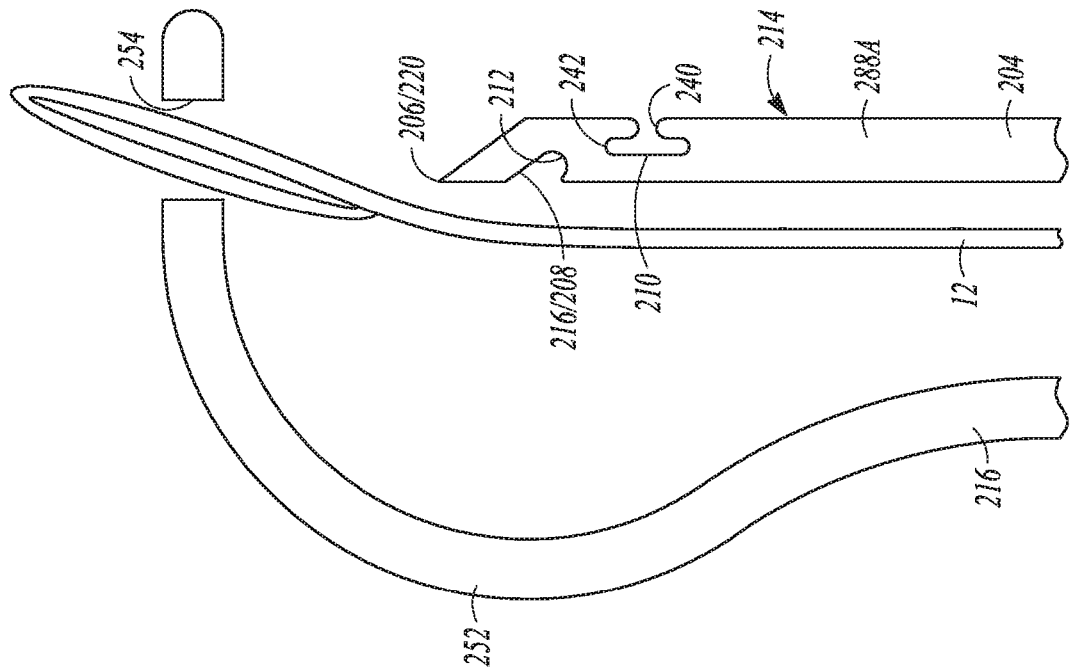
Figure 9D:
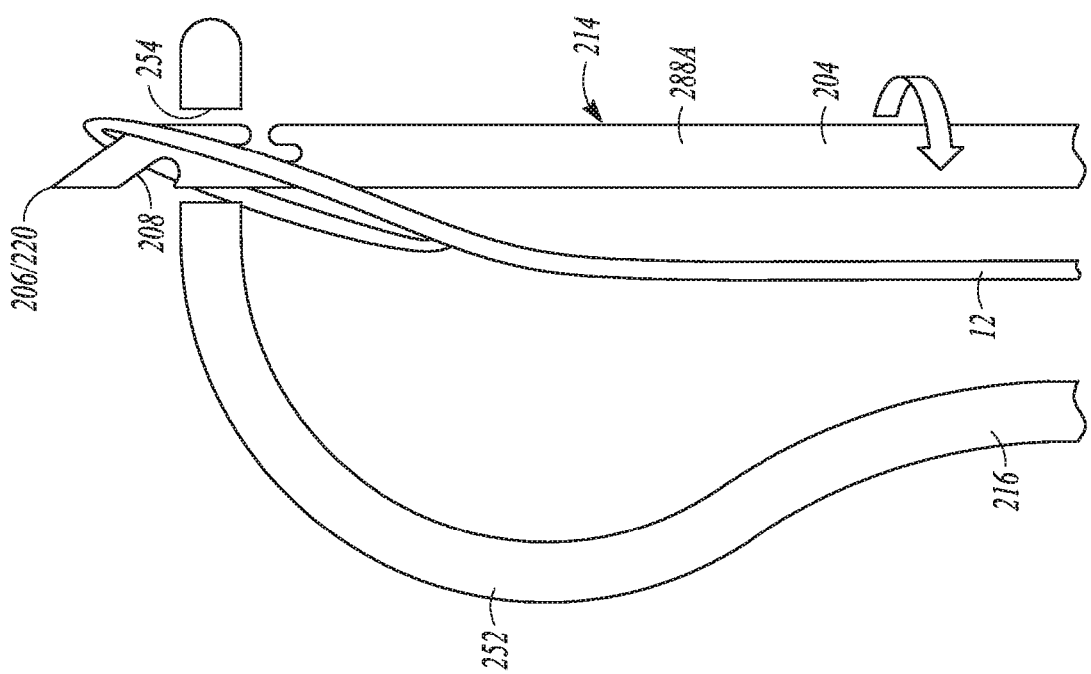

During surgery, movable needle 288a can be used similarly to movable needle 88a for repairing soft tissue, except that movable needle 288a can be rotated within eyelet 254 of fixed needle member 216 during the repair. As an example, movable needle 288a can be moved into eyelet 254 with suture 12 within hook member 208 to drive suture 12 through eyelet 254 (FIGS. 9A-B). Then, as shown in FIGS. 9C-D, movable needle 288a can be rotated about its longitudinal axis within eyelet 254 (e.g., by anywhere between about 90-270°, and more preferably 180°) to disengage suture 12 from hook member 208. Subsequently, movable needle 288a can be withdrawn from eyelet 254 with suture 12 still retained in eyelet 254. Indeed, eyelet 254 can have suture-retaining features similar to eyelet 54 (e.g., opposed ends 78 of openings 72), although not shown.

Figure 9F:
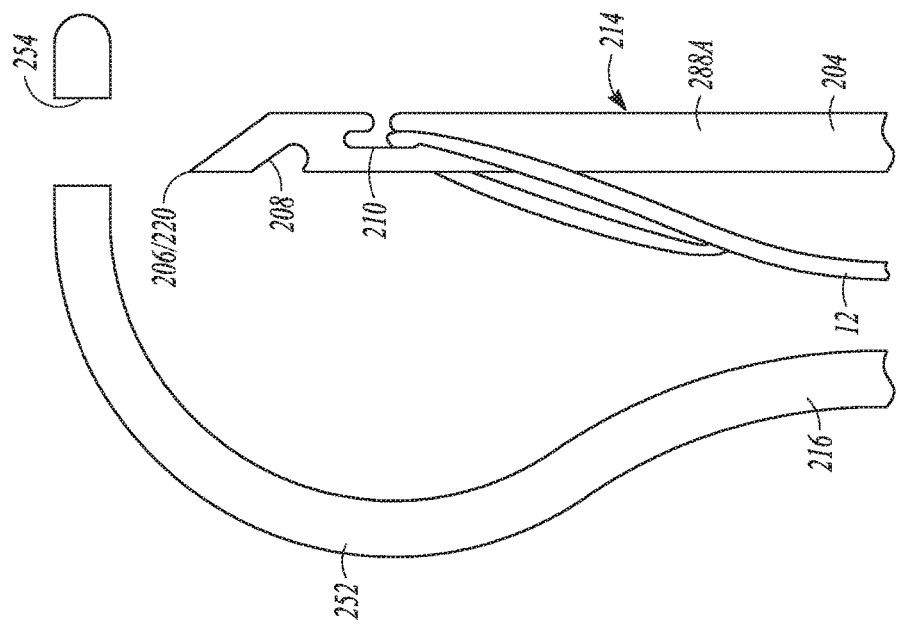
Figure 9E:
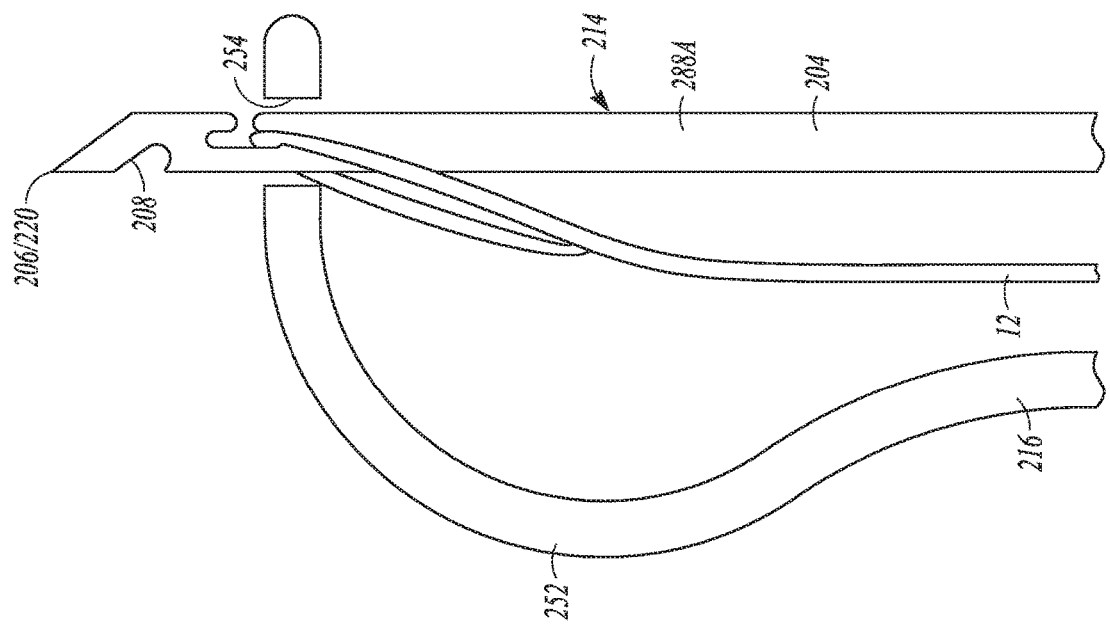

Eyelet 254 can then be moved to another location as described above with respect to the main embodiment, and then movable needle 288*a* can be reinserted into eyelet 254 to grasp and withdraw suture 12. In this way, the alternate suture passing instrument can be used similar to the main embodiment discussed above to form a mattress stich without removing the alternate suture passing instrument from the joint. In an example, hook member 210 can be used to grasp suture 12 as it is inserted into eyelet 254, as shown in FIGS. 9E-F. Suture 12 can be moved through small opening 240 and into larger opening 242 of hook member 210. Suture 12 can then be withdrawn from the soft tissue and a mattress stich formed to reduce any tear(s) in the tissue, as described above with respect to the main embodiment. Thus, alternate movable needle 288*a* can be used similarly to movable needle 88*a* of the main embodiment above, except movable needle 288*a* can use a unique rotating technique within eyelet 254, as described.

Although movable needle 288*a* is not described directly as being usable as a substitute for movable needle 88*a* of suture passing instrument 10, it is to be understood that the disclosure contemplates just that, with some modifications being made to suture passing instrument 10 to accommodate the rotational features of movable needle 288*a*. For example, while movable needle 88*a* can be directly connected to first slide member 32, and first slide member 32 can move longitudinally, it is contemplated that a different slide member can be substituted for first slide member 32 that has rotational capabilities. For instance, a different slide member could be provided with suture passing instrument 10 that can rotate within handle 14 during use. A separate actuator (e.g., a rotatable knob on handle 14) could be provided to rotate such a substitute slide member. In addition, the substitute slide member could be attached to movable needle 288*a* and, when rotated, could act to rotate movable needle 288*a* in the manner described herein. Other rotation mechanisms are also possible as modifications to suture passing instrument 10 for use with movable needle 288*a*. Thus, the disclosure contemplates that suture passing instrument 10 can be modified to suit the rotational needs of movable needle 288*a*, thereby providing a second suture passing instrument. The second suture passing instrument can be used in the manner described above, similar to suture passing instrument 10 of the main embodiment, to repair soft tissue.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A suture passer comprising:
    a first needle extending along a first longitudinal axis, wherein the first needle has a sharp a first hook member configured to grasp a first portion of a suture and a second hook member configured to grasp a second portion of the suture, wherein the first hook member is positioned on a first side of the first needle, and the second hook member is positioned on a second side of the first needle;
    a shaft extending along a second longitudinal axis, wherein the shaft has an eyelet that intersects with the first longitudinal axis of the first needle; and
    an actuation mechanism coupled to the first needle, wherein actuating the actuation mechanism moves the first needle to a position in which the first needle's sharp tip extends through the eyelet, and releasing the actuation mechanism moves the first needle to a position in which the first needle's sharp tip is a spaced apart a distance proximal of the eyelet.

2. The suture passer of claim 1, wherein the shaft comprises a second needle with a sharp tip.

3. The suture passer of claim 1, wherein the shaft comprises a first straight section extending along the second longitudinal axis, and a second curved section diverging from the second longitudinal axis.

4. The suture passer of claim 3, wherein the eyelet is located on the second curved section of the shaft.

5. The suture passer of claim 1, wherein the eyelet comprises at least a first opening that is configured to retain a portion of the suture therein.

6. The suture passer of claim 1, wherein the first longitudinal axis is substantially parallel to the second longitudinal axis.

7. A method of repairing soft tissue comprising:
    positioning an eyelet of a suture passer at a first position relative to a tear in soft tissue of a patient, the eyelet being located on a shaft that extends along a first longitudinal axis;
    engaging suture with a first needle of the suture passer by engaging the suture with a first hook member of the first needle, and moving the first needle and the suture engaged thereto by way of the hook member through the eyelet so that the suture couples to the shaft, the needle having a sharp tip and a needle body that extends along a second longitudinal axis;
    puncturing the soft tissue with the sharp tip of the needle along a first path through the tissue, and subsequently moving the first needle and the suture engaged thereto through the eyelet so that the suture couples to the shaft;
    withdrawing the first needle from the eyelet and through the soft tissue along the first path while leaving the suture coupled to the shaft;
    moving the eyelet from the first position to a second position relative to the tear in the soft tissue;
    puncturing the soft tissue with the sharp tip of the needle along a second path through the tissue, and subsequently (i) moving the first needle through the eyelet, and (ii) capturing the suture with the first needle with a second hook member of the first needle, and withdrawing the suture through the soft tissue along the second path by moving the first needle with the suture attached thereto by way of the second hook member through the soft tissue along the second path; and
    reducing the tear in the soft tissue using the suture.

8. The method of claim 7, wherein the first longitudinal axis is substantially parallel to the second longitudinal axis.

9. The method of claim 7, wherein the shaft comprises a first straight section extending along the second longitudinal axis, and a second curved section diverging from the second longitudinal axis.

10. The method of claim 9, wherein the eyelet is located on the second curved section of the shaft.

11. The method of claim 7, further comprising rotating the first needle within the eyelet prior to withdrawing the first needle from the eyelet.

12. The method of claim 7, further comprising engaging a portion of the suture with an opening in the eyelet to couple the suture to the eyelet.

13. A suture passer comprising:
- a first needle extending along a first longitudinal axis, wherein the first needle has a sharp a first hook member configured to grasp a first portion of a suture and a second hook member configured to grasp a second portion of the suture, wherein the first hook member is positioned on a first side of the first needle, and the second hook member is positioned on a second side of the first needle;
- a shaft extending along a second longitudinal axis, wherein the shaft has an eyelet that intersects with the first longitudinal axis of the first needle; and
- an actuation mechanism coupled to the first needle, wherein the actuation mechanism is configured to rotate the first needle about the first longitudinal axis, and wherein actuating the actuation mechanism moves the first needle to a position in which the first needle's sharp tip extends through the eyelet, and releasing the actuation mechanism moves the first needle to a position in which the first needle's sharp tip is a spaced apart a distance proximal of the eyelet.

14. The suture passer of claim 13, wherein the shaft comprises a first straight section extending along the second longitudinal axis, and a second curved section diverging from the second longitudinal axis.

15. The suture passer of claim 14, wherein the eyelet is located on the second curved section of the shaft.

16. The suture passer of claim 13, wherein the first needle is rotatable when positioned inside the eyelet to place the first needle in a removal orientation.

\* \* \* \* \*

UNITED STATES PATENT AND TRADEMARK OFFICE
CERTIFICATE OF CORRECTION

PATENT NO. : 10,980,532 B2
APPLICATION NO. : 16/312592
DATED : April 20, 2021
INVENTOR(S) : Norton et al.

It is certified that error appears in the above-identified patent and that said Letters Patent is hereby corrected as shown below:

In the Claims

In Column 11, Line 66, in Claim 1, after "sharp", insert --tip,--

In Column 13, Line 11, in Claim 13, after "sharp", insert --tip,--

Signed and Sealed this
Sixth Day of July, 2021

Drew Hirshfeld
*Performing the Functions and Duties of the
Under Secretary of Commerce for Intellectual Property and
Director of the United States Patent and Trademark Office*